US00PP26646P2

(12) United States Plant Patent
Lane et al.

(10) Patent No.: US PP26,646 P2
(45) Date of Patent: Apr. 26, 2016

(54) ***PRUNUS* TREE NAMED '13S2101'**

(50) Latin Name: *Prunus avium*
Varietal Denomination: 13S2101

(71) Applicant: Her Majesty The Queen In Right Of Canada as Represented by the Minister of Agriculture and Agri-Food, Ottawa (CA)

(72) Inventors: William David Lane, Summerland (CA); Richard MacDonald, Summerland (CA)

(73) Assignee: Her Majesty the Queen in Right of Canada as Represented by the Minister of Agriculture and Agri-Food, Ottawa (CA)

( * ) Notice: Subject to any disclaimer, the term of this patent is extended or adjusted under 35 U.S.C. 154(b) by 125 days.

(21) Appl. No.: 13/999,463

(22) Filed: Mar. 3, 2014

Related U.S. Application Data

(60) Provisional application No. 61/852,334, filed on Mar. 15, 2013.

(51) Int. Cl.
*A01H 5/00* (2006.01)

(52) U.S. Cl.
USPC ..... Plt./181

(58) Field of Classification Search
USPC ..... Plt./181
See application file for complete search history.

(56) References Cited

PUBLICATIONS

PLUTO Plant Variety Database Jul. 22, 2015. p. 1.*

* cited by examiner

*Primary Examiner* — Annette Para
(74) *Attorney, Agent, or Firm* — Penny J. Aguirre

(57) ABSTRACT

A new cultivar of *Prunus avium*, '13S2101', characterized by its very late harvest season, its flowers that are self-fertile, its moderate precocity of fruit bearing, its spreading growth habit with horizontal one year-old shoots, its fruit skin and flesh that is red color with juice that is high in sweetness, and its firm fruit that is elongate to cordate in shape.

1 Drawing Sheet

Botanical classification: *Prunus avium.*
Variety denomination: '13S2101'.

BACKGROUND OF THE INVENTION

The present invention relates to a new and distinct cultivar of *Prunus avium* and will be referred to hereafter by its cultivar name, '13S2101'. '13S2101' is a new cultivar of sweet cherry tree grown for fruit production.

The new cultivar of *Prunus* arose from a breeding program conducted by the Inventor at a research centre in Summerland, BC, Canada with the goal of developing a new cultivar of cherry tree that would extend the harvest season with fruit that was firm and well-sized with good stem pull retention and good storage life and flowers that are self-fertile.

'13S2101' originated as a seedling that arose from seed planted from open pollination of 'Sweetheart' (not patented) in 1982. '13S2101' (breeding ref no. 13S-21-01) was selected as a single unique tree in 1991 from amongst the resulting seedlings.

Asexual propagation of the new cultivar was first accomplished by budding onto *Prunus avium* rootstock by the Inventor in Summerland, BC, Canada in 1991. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar as grown in test plots in Summerland, BC, Canada. These attributes in combination distinguish '13S2101' as a unique cultivar of cherry tree.

1. '13S2101' exhibits a very late harvest season; August $11^{th}$ in Summerland, BC, Canada.
2. '13S2101' exhibits flowers that are self-fertile.
3. '13S2101' exhibits a moderate precocity of fruit bearing.
4. '13S2101' exhibits a spreading growth habit with horizontal one year-old shoots.
5. '13S2101' exhibits fruit that is firm with red skin and flesh with juice that has a high degree of sweetness.
6. '13S2101' exhibits fruit that is elongated to cordate in shape.

'Sweetheart', the female parent, is similar to '13S2101' in being self-fertile but differs from '13S2101' in having a tree habit that is more upright, in having round shaped fruit, higher fruit set, and a fruit harvest maturity date at least 10 days earlier. '13S2101' can be most closely compared to the cultivars '13S2009' (U.S. Plant Pat. No. 20,551) and 'SPC103' (U.S. Plant Patent pending). '13S2009' is similar to 'SPC103' in being self-fertile but differs '13S2101' in having fruit that is compressed cordate in shape with a higher fruit set, and a fruit harvest maturity date that is about 4 days earlier. 'SPC103' is similar to '13S2101' in having a late harvest day, however 'SPC103' differs most significantly from '13S2101' in having fruit that is dark red-purple in color and kidney to cordate in shape.

BRIEF DESCRIPTION OF THE DRAWING

The accompanying colored photograph illustrates the overall appearance and distinct characteristics of the fruit of '13S2101' on an 8 year-old tree as grown in a trial plot in Summerland, BC, Canada.

The photograph in FIG. 1 provides a view of a cluster of fruit of '13S2101'. The colors in the photograph are as close as possible with the digital photography techniques available, the color values cited in the detailed botanical description accurately describe the colors of the cherry tree.

DETAILED BOTANICAL DESCRIPTION

The following is a detailed description of 8 year-old trees as grown in a trial plot in Summerland, BC, Canada. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Plant type*.—Deciduous fruit bearing tree.

*Plant habit*.—Spreading with horizontal branching.

*Height and spread*.—Reaches about 3.20 m in height and about 3.76 m in width.

*Cold hardiness*.—U.S.D.A. Zone 4.

*Diseases and pests*.—No susceptibility or resistance to diseases or pests has been observed.

*Root description*.—Fibrous, freely branched.

*Propagation*.—Budding onto rootstock.

*Growth rate*.—Moderate.

Trunk description:

*Size of trunk*.—23.6 cm in diameter measured 38 cm above soil level.

*Bark color*.—202D with horizontal streaks of 184B.

*Bark texture*.—Rough and peeled.

Description of dormant shoots (one year-old):

*Pubescence*.—Absent or very weak.

*Shoot size*.—Average of 31 cm in length and 6.22 mm in width.

*Anthocyanin presence*.—Weak.

*Thickness of shoot at center of middle internode*.—Thin to moderate; average of 4.57 mm.

*Bark color*.—174A.

*Shoot angle*.—Nearly horizontal.

*Lenticels*.—13.3 lenticels per 2 $cm^2$.

*Branch internode length*.—Moderately long; average of 40 mm.

*Vegetative buds*.—Large in size; 7.90 mm in length and 3.88 mm in width, conical in shape, held slightly out from shoot, support is moderately high.

Description of growing shoots:

*Color of growing tip of shoot*.—174A.

*Pubescence of shoots tip*.—Absent or very weak.

*Anthocyanin presence*.—Weak.

Foliage description:

*Leaf shape*.—Elliptic.

*Leaf division*.—Simple.

*Leaf base*.—Rounded.

*Leaf apex*.—Acute and acuminate to cuspidate at very tip.

*Leaf fragrance*.—None.

*Leaf burst*.—Early in the beginning of full flowering.

*Leaf venation*.—Pinnate, not prominent, same as leaf color with the midrib on lower surface.

*Leaf margins*.—Dentate.

*Leaf arrangement*.—Alternate.

*Leaf aspect*.—Concave and held horizontal to slightly downward in relation to shoot.

*Leaf attachment*.—Petiolate.

*Leaf surface*.—Slightly pubescent on lower surface with upper surface moderately glossy.

*Leaf size*.—Mature leaves average 17 cm in length and 8.6 cm in width.

*Leaf internodes*.—Average of 3.8 cm.

*Leaf color*.—Mature leaves upper surface; 139A, mature leaves lower surface; 137C, fall color occurs late in season.

*Petioles*.—Average of 3.64 cm in length and 2.50 mm in width, 174A in color with anthocyanin's, typically 3 nectaries that are kidney-shaped and 166A in color, glabrous surface.

Inflorescence description:

*Blooming period*.—Blooms about mid-late in the bloom season in B.C., Canada, just after '13S2009'.

*Inflorescence type*.—Clusters of single flowers.

*Lastingness of inflorescence*.—Average of 7 to 10 days.

*Flower buds*.—Ovoid, sharp tip in shape, about 7.8 mm in length and 3.36 mm in width prior to opening, 166A in color.

*Flower quantity*.—Medium density.

*Flower type*.—Rotate corolla above an elongated calyx with stamens and pistil extended.

*Flower size*.—Large; average of 4.23 cm in diameter.

*Calyx*.—Comprised of sepals fused into an ovoid base with un-fused portions spreading at apex.

*Sepals*.—5, 180C in color, glabrous surface, about 5.97 mm in length, entire glandular margin, attenuate apex, fused base.

*Petals*.—5, round in shape, un-fused, overlapping, smooth margin, rounded base, rounded apex, about 16.24 mm in length and 9.37 mm in width, 155C in color (upper and lower surface).

*Pedicels*.—Average of 35.89 mm in length, 0.89 mm in width, 143B in color, glabrous surface.

*Rachis*.—Glabrous surface, flowers lightly compacted with whorled arrangement.

Reproductive organs:

*Gynoecium*.—1 pistil about 11.95 mm in length and 1 mm in width extending beyond perianth, style is 167A in color, stigma is about 1 mm in diameter and 142B in color, ovary is superior, glabrous and 141C in color.

*Androcoecium*.—Average of 28 stamens, base adnate to calyx, filaments are 161D in color, about 13.30 mm in length and 1 mm in width, anthers are 166B in color, dorsifixed, about 0.5 mm in length and in width, pollen is abundant in quantity and about 166B in color.

*Fertility*.—Self-fertile.

Fruit description:

*Fruit type*.—Drupe.

*Fruit shape*.—Kidney-shaped (lateral view is flattened to rounded), flat to pointed apex.

*Fruit apex*.—Flat and slightly protruding with moderately low susceptibility to rain induced cracking.

*Fruit size*.—Very large; 24.29 mm in length and 27.15 mm cm in width.

*Fruit firmness*.—Firm.

*Fruit set*.—Medium.
*Fruit stalk*.—Long; average of 5.54 cm in length and 1.32 mm in width, surface, color 138B.
*Fruit bearing*.—Medium.
*Skin color*.—59A when ripe with light colored dots.
*Skin suture*.—Low prominence.
*Harvest date*.—Very late harvest season; August 11$^{th}$ in Summerland, BC, Canada, 31 days after Bing.
*Skin surface*.—Glossy.
*Flesh color*.—53B.
*Flesh texture*.—Fleshy, moderately juicy.
*Flavor*.—High degree of sweetness.
*Weight*.—An average of 10.7 g/drupe.
*Brix*.—20.6.
*Acidity*.—pH 3.69.
*Storage life*.—Up to 4-5 weeks at 0.5° C.
*Seeds*.—1 stone per drupe, 159B in color, large in size; average of 10.56 mm in length and 9.57 mm in width, 7.81 mm thick, semi adherent to flesh, shape; lateral view is symmetrical and spherical to elongate, front view is ovate, basal view is round, keel is moderately developed.

It is claimed:

1. A new and distinct cultivar of *Prunus* tree named '13S2101' as herein illustrated and described.

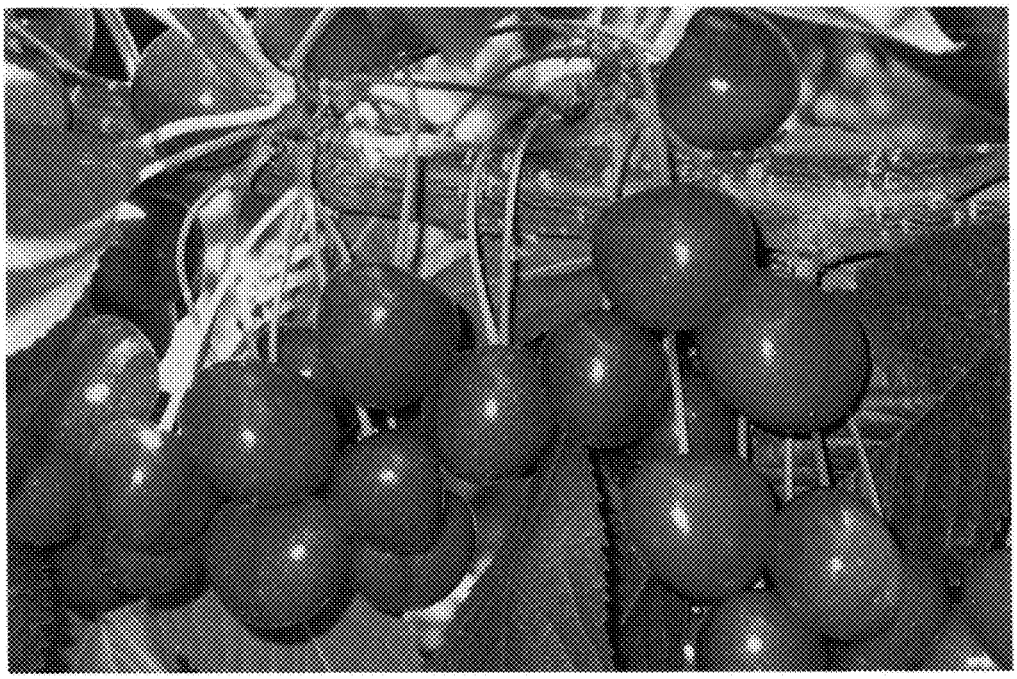

* * * * *